United States Patent
Elfström et al.

(10) Patent No.: US 7,553,300 B2
(45) Date of Patent: Jun. 30, 2009

(54) ABSORBENT PRODUCT FOR MEN

(75) Inventors: Anna-Carin Elfström, Torslanda (SE); Cécile Sandin, Mölndal (SE); Kenneth Strannemalm, Floda (SE)

(73) Assignee: SCA Hygiene Products AB, Gothenburg (SE)

( * ) Notice: Subject to any disclaimer, the term of this patent is extended or adjusted under 35 U.S.C. 154(b) by 1041 days.

(21) Appl. No.: 10/612,154

(22) Filed: Jul. 3, 2003

(65) Prior Publication Data

US 2004/0097893 A1    May 20, 2004

Related U.S. Application Data

(60) Provisional application No. 60/393,598, filed on Jul. 5, 2002.

(51) Int. Cl.
*A61F 5/44* (2006.01)

(52) U.S. Cl. ........................ 604/353; 604/349

(58) Field of Classification Search ............ 604/385.03, 604/347, 349–353; 2/403–405
See application file for complete search history.

(56) References Cited

U.S. PATENT DOCUMENTS

| | | | |
|---|---|---|---|
| 4,023,216 A * | 5/1977 | Li | 4/144.3 |
| 4,675,012 A * | 6/1987 | Rooyakkers | 604/349 |
| 5,486,168 A * | 1/1996 | Runeman et al. | 604/385.26 |
| 5,558,734 A | 9/1996 | Sherrod et al. | |
| 5,810,799 A | 9/1998 | Slater | |
| 6,023,789 A * | 2/2000 | Wilson et al. | 2/228 |
| 7,172,585 B2 | 2/2007 | Sandin et al. | |
| 2003/0125690 A1* | 7/2003 | Hermansson et al. | 604/385.01 |
| 2003/0181883 A1* | 9/2003 | Olson et al. | 604/385.01 |

FOREIGN PATENT DOCUMENTS

| | | |
|---|---|---|
| EP | 0 225 909 B1 | 6/1987 |
| WO | 96/05786 | 2/1996 |
| WO | 99/42066 | 8/1999 |

* cited by examiner

*Primary Examiner*—Tatyana Zalukaeva
*Assistant Examiner*—Melanie J Hand
(74) *Attorney, Agent, or Firm*—Buchanan Ingersoll & Rooney PC

(57) ABSTRACT

An absorbent product for men, having an absorption body (5) which tapers from a front section (11) of the product towards a crotch section (12) of the product and which is enclosed in a sheath including a liquid-tight layer (4) and a liquid-permeable layer (3), both of which layers extend beyond the absorption body round about this and are mutually joined there. The absorption body (5) is arranged to extend, during product usage, from the front section of the product in the direction of the crotch section and is adapted to extend with its narrower end section to slightly below the penis of the user. On the liquid-permeable layer (3), at the narrower end section of the absorption body, a liquid barrier (17) is applied, which is arranged to prevent urine emitted by the user from leaking from the surface of the absorption body towards the crotch region.

36 Claims, 7 Drawing Sheets

ABSORBENT PRODUCT FOR MEN

CROSS-REFERENCE TO RELATED APPLICATIONS

The present application claims the benefit of U.S. Provisional Application No. 60/393,598, filed in the United States on Jul. 5, 2002, the entire contents of which are hereby incorporated herein by reference.

BACKGROUND OF THE APPLICATION

1. Technical Field

The present invention relates to an absorbent product for men, comprising an absorption body which tapers preferably towards one end from a front section of the product towards a crotch section of the product and which is enclosed in a sheath consisting of a liquid-tight layer on the side of the absorption body facing away from the user during use and a liquid-permeable layer on the opposite side of the absorption body, both of which layers extend beyond the absorption body round about this and are mutually joined there, and the absorption body is arranged to extend, during product usage, from the said front section of the product in the direction of the crotch region and is intended to extend with its narrower end section to slightly below the penis of the user.

2. Background Art

In practice, conventional diapers have hitherto commonly been used as incontinence pads for men. The drawback with conventional diapers is that they are intended to absorb both urine and faeces and that they are therefore not suitable for men who only need a urine-collecting pad. Conventional diapers are relatively cumbersome, having thick and wide absorption bodies which, during usage, extend the whole of the way from the abdominal section of the user, through the crotch and a substantial way up over the back of the user. Large and bulging diapers are not, of course, suitable, especially not for men who have urine incontinence but who are not in any way handicapped. For reasons of both comfort and modesty, there is a great need for more purposeful products for incontinent men.

Light incontinence is a large and hidden handicap from which many men suffer and which seriously limits their chance of leading a normal active life. A large group of men who suffer from this are those with prostate problems. Following surgery, these men are usually afflicted by drip incontinence, which causes a great deal of suffering.

Incontinence pads for men with light incontinence are previously known per se, but they have not worked satisfactorily in all respects. Examples of previously known incontinence pads for men are pads of the type which have a container-like part for receiving the genitals of the male user. Fundamental drawbacks with these are that they are altogether too warm, at the same time as they are too tight-fitting and hence uncomfortable for the user. A further drawback with pads of this type is that they are too rigid and can give rise to chafing.

Swedish patent specification SE 450 811 describes an incontinence pad intended for men, consisting of an upper shield-like part, which, during usage of the pad, is applied over the penis and scrotum of the user, and a lower part, which, during usage of the pad, curves inwards under the penis and scrotum without totally surrounding these and has a downward-tapering cup-like shape. The pad according to the said publication is airy and relatively comfortable compared with conventional diapers. Unlike the abovementioned incontinence pads having a container-like part, it does not enclose the organs of the user, but instead forms an airy splash guard. The configuration of the pad with a downward-tapering, cup-like part provides, in addition to good adjustment of the pad to the body of the user, at the same time a guard for downward splashes.

The pad according to the publication is formed from a flat blank, the one end of which has two separate longitudinal flaps. The cup-like lower part of the pad is obtained by the said flaps being curved and mutually connected in somewhat overlapping arrangement.

A drawback with these previously known incontinence pads is that the production process is relatively complicated with cutting steps, folding steps and connecting steps. Another drawback is that the pad, in order to work fairly reliably, should have a good fit for the respective user, which, with this design, is unattainable in practice since the size of different users naturally varies considerably and it is not economically possible to have a satisfactory range of sizes. A further drawback is that the incontinence pad according to SE 450811, in order to be able to assume the desired cup-like shape at the bottom, limits the choice of material in the pad, since this must have relatively high stiffness in order to assume and maintain the desired cup shape.

Another example of a previously known incontinence pad for men is described in U.S. Pat. No. 5,486,168. This pad has an absorption body which tapers towards one end from a front section of the product towards a crotch section of the product and which is enclosed in a sheath consisting of a liquid-tight layer on the one side of the absorption body and a liquid-permeable layer on the opposite side of the absorption body. The two layers extend beyond the absorption body and are mutually joined there. The incontinence pad according to the last-named publication is provided with elastic threads or the like, which are applied with pretensioning to the sheath on both sides of the absorption body and which converge in the direction of the narrower end section of the absorption body. The absorption body has lower flexural stiffness transversely to the transverse direction the closer one gets to the narrow end of the absorption body and the elastic threads will therefore lend the absorption body increased curvature the closer one gets to the narrow end. The elastic and the tapered absorption body interact to give the pad a cup-like part at the bottom, which cup-like part, during usage of the pad, is intended to arc in under the penis and scrotum of the user.

In a configuration according to U.S. Pat. No. 5,486,168, it is important for the absorption body to have a stiffness which enables the absorption body to interact with the elastic as intended, thereby limiting the choice of materials for the absorption body. A further drawback with the design according to the last-named patent publication is that any variances in stiffness per unit of area over the surface of the absorption body can give rise to unwanted folds in the lateral direction out from the absorption body, which in turn can lead to urine leakage along the folds in the lateral direction out from the product. Another drawback is that incontinence pads according to U.S. Pat. No. 5,486,168 are difficult to pack in the compressed state, since there is a high risk of the three-dimensional products formed by the elastic being destroyed in the packaging operation or during storage in the packaging. The tension from the elastic of the absorption body, in combination with external mechanical influences, results in both the elastic and the absorption body being subjected to high stresses.

OBJECTS AND SUMMARY

There has long been a great need for discrete, comfortable and effective incontinence pads for men with light incontinence, such as drip incontinence. No products have emerged which are satisfactory in every respect. There is a large known group of men with light incontinence who would need more practical products to be able to lead a normal active life without being fearful of urine leakage and feeling that the pads which are worn are visible or perceptible outside the clothes of the user.

It is also known that there is a very large group of men who have not sought care for their incontinence problems and whose problems are not related to previous surgery. The size of this group is not known, but studies in certain countries show that light incontinence is a very widespread problem and that the need for effective, discrete and comfortable products is very great.

As a result of the present invention, a product of the type stated in the introduction has been produced, by means of which the above-stated problems have been reduced or totally eliminated. To this end, according to an embodiment of the invention, on the liquid-permeable layer, at the narrower end section of the absorption body, a liquid barrier is applied, which is arranged to prevent urine emitted by the user from leaking from the surface of the absorption body towards the crotch region of the user.

According to one embodiment, the absorbent product is an insert intended for use in combination with underpants and, to this end, the product is provided with one or more fastening members on the outer side of the liquid-tight layer, which fastening members are intended to hold the absorbent product in its intended place inside the pants.

According to another embodiment, the product as a whole has a pants-like shape having a front section, a rear section and a crotch section, the front section and rear section being intended to surround the waist of the user, and the front and/or rear section is provided with waist elastic, which is intended to hold an applied product in place on the user.

According to another embodiment, the front section has at least one elastic member, which, during product usage, enables the front section of the product to be pulled down, counter to the action of the said elastic member, to a position in which the upper limit edge of the front section in the middle region of the front section is situated below the penis of the user, at the same time as the upper limit edge of the front section in the two outer edge regions of the front section is arranged to be held in place around the waist of the user, the absorbent material is configured with one or more deformation zones, which enable those parts of the absorption body which, during product usage, are situated above and over the penis of the user to be drawn down together with the rest of the front section when the front section of the product is pulled down, and the front section of the product and the absorption body are arranged to be returned by the elastic member to their original usage position.

In previously known incontinence pads for men, the user has, in practice, been unable to visit urinals. It is naturally inconceivable for a man, in connection with a toilet visit at a urinal, to pull down a whole incontinence pad and thereby reveal private and embarrassing problems to those around him. With a pad according to the last-named embodiment, this problem has been eliminated.

According to a further illustrative embodiment of the invention, the waist elastic is formed from an elastic first piece which, in the extended state, is essentially rectangular and which is intended to partially surround the trunk of the user and form the rear section and side sections of the pants-like product, a second piece, incorporated in the product, is configured to form the front section and crotch section of the pants-like product, the second piece is elongated with two opposing end edges and two opposing longitudinal edges, the width of the second piece, at least at the crotch section, is less than the length of the first piece, the second piece with its longitudinal direction is arranged perpendicularly to the longitudinal direction of the first piece and is connected by a first end section to the one longitudinal edge section of the first piece and centrally on this, the one end section of the first piece is connected to a first side edge section of the second piece, and the second end section of the first piece is correspondingly connected to a second side edge section of the second piece, and the absorbent element is applied, in its entirety, on the second piece.

By virtue of the fact that the whole of the rear section is elastic and, together with the elastic side sections, forms a single elastic continuous first piece, the pants as a whole are very responsive to body movements. Local disturbances are absorbed and smoothed out by the continuous elastic piece and are not transmitted to the less resilient parts of the front section and crotch section situated directly in front of the genitals of the user. Compared with conventional diapers and previously known pants-shaped absorbent products, with the product according to the present invention a superior fit and comfort are obtained. The greater part of the pants-like garment remains totally plain. The seams which are needed are applied at the transition between the front section and the first piece and at the transition between the first and second piece at the crotch section. These seams end up in places which are not subjected to any great pressure during product usage and there is less risk of chafing and pressure sores caused by seams on the pants-like product.

The embodiment of the absorbent product according to the invention from only two part-pieces and in which the absorption body is situated entirely on the second part-piece offers increased freedom in the choice of production method compared with previously known pants-shaped products. The prospect of freely choosing suitable materials on different parts of the absorbent product is also substantially increased compared with conventional pants-like absorbent products produced with outer layers configured in a single piece.

According to one embodiment, the liquid barrier is arranged to follow the contour of the lower, narrower end section of the absorption body and is applied in its entirety inside the said contour.

According to another embodiment, the liquid barrier crosses the absorption body close to its narrower end and in that the liquid barrier is convex in the direction of the said end.

According to a further embodiment, the liquid barrier extends in the lateral direction beyond the absorption body and in the transverse direction spans the whole of the absorbent product. This configuration can be simpler from the production aspect compared with a design in which the liquid barrier only crosses the actual absorption body.

According to another embodiment, the liquid barrier, at least during product usage and at least close to the middle of the absorption body in the transverse direction, has a height of at least 5 mm, preferably 10-20 mm. The liquid barrier can therefore, within the scope of the invention, always assume the height or be configured such that the liquid barrier is raised when the user dons the product and, in so doing, bends it somewhat.

According to one embodiment, the liquid barrier is fixed in the rest of the absorbent product only along its outer edge section and in that inner-situated sections of the liquid barrier are arranged to be raised from the liquid-permeable layer during product usage.

According to another embodiment, the liquid barrier is constituted by a roll formed from one or more band-shaped materials, which roll is bent into the desired convex shape in the direction of the narrower end of the absorption body.

According to another embodiment, the liquid barrier is constituted by a number of circumferential folds of one or more band-shaped materials, which liquid barrier, following the formation of the folds, is elongated in the direction of the fold lines forming the folds, and in that the liquid barrier is folded or bent into the desired shape.

According to one embodiment, the elongated liquid barrier is folded in the middle along a transverse oblique line, such as at an angle of 45°, in relation to the longitudinal direction to form a V-shaped liquid barrier with the point of the V against the crotch section.

According to a somewhat modified embodiment, the elongated liquid barrier is folded at two places along transverse lines along an acute angle, viewed from the lower limit edge of the liquid barrier in the applied position, to form an essentially U-shaped liquid barrier with the base of the U against the crotch section.

According to one embodiment, the band material incorporated in the liquid barrier is constituted by non-woven, preferably hydrophobic non-woven material, or by a laminate of non-woven material and a plastics film.

According to another embodiment, the liquid barrier is constituted by a single material strip, for example a hydrophobic non-woven material, which has been folded or bent into suitable shape before being applied.

According to a further embodiment, the liquid barrier, on its free longitudinal edge section, is provided with a pretensioned longitudinal elastic element, such as an elastic thread, which element is intended to hold the liquid barrier in the raised state during product usage.

According to another embodiment, the liquid barrier has an inherent stiffness of such magnitude that a liquid barrier applied in the folded or bent state, by virtue of its own inherent stiffness in the said bent or folded state during product usage, is held with its free longitudinal edge section in the raised state.

According to a further embodiment, the absorption body is formed from cellulose fluff, possibly with highly absorbent material mixed in, and the liquid barrier is constituted by a moulding, which is formed from air-laid fibers such as cellulose fluff, and this moulding is applied so that it follows the contour of the narrower end section of the absorption body on or directly outside this.

According to another embodiment, the liquid barrier is constituted by a foam material which has been cast or folded into the desired shape.

BRIEF DESCRIPTION OF DRAWINGS

The invention will be described in greater detail below with reference to illustrative embodiments shown in the appended drawings, in which.

DETAILED DESCRIPTION OF THE PREFERRED EMBODIMENTS

Figure 1:
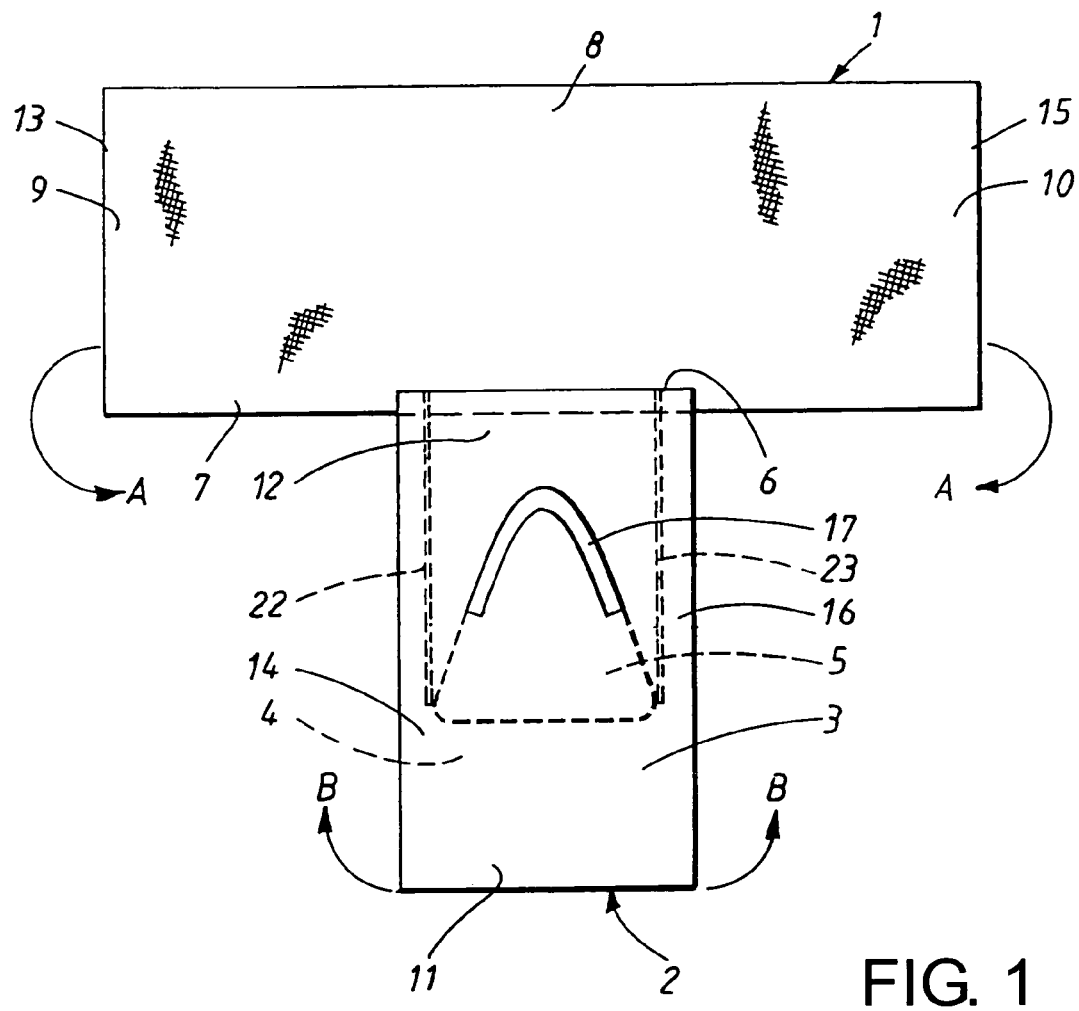
FIG. 1 shows diagrammatically in flat form a phase in the development of an absorbent product according to a first embodiment of the invention.

As can be seen from FIG. 1, the embodiment according to FIG. 1 comprises a first piece 1. This is elastically stretchable and is shown in FIG. 1 in a flat and evenly extended state, in which the elastic piece 1 is essentially rectangular. The elastic first piece 1 can be formed from conventional materials familiar to the person skilled in the art, such as woven elastic materials, elastic non-wovens or elastic films. The elastic piece is stretchable for a user when putting on the product and it fits tight with suitable tightening around the user when the article is worn. The tightening is adjusted, of course, by means of size and elastic stretchability.

The product incorporates a second piece 2, consisting of an inner layer 3, an outer layer 4 and an absorption body 5 applied between these. In the embodiment shown in FIG. 1, this is in a flat form essentially triangular. The choice of material in the absorption body is not critical but can be chosen from amongst materials or material combinations familiar to the person skilled in the art. For example, the absorption body can be made up of cellulose fluff with superabsorbent material in powder or fibre form mixed in with this. The outer layer 4 can consist, for example, of a polyethylene film of a type conventionally used for absorbent products. A liquid-tight film in combination with an outer fibre layer is suitable if an absorbent product having a more textile-like appearance is sought. The inner layer 3 can be formed from a liquid-permeable non-woven material. The outer layer and the inner layer extend with sections beyond the absorption body and are mutually connected in these sections. The second piece 2 is elongated and is applied with its longitudinal direction perpendicular to the longitudinal direction of the first piece 1. The second piece 2 is connected by an end section 6 to the one longitudinal edge section 7 of the first piece 1 and centrally on this. The connection can be realized, for example, by the use of bonding agent, heat bonding or ultrasonic bonding.

Figure 2:
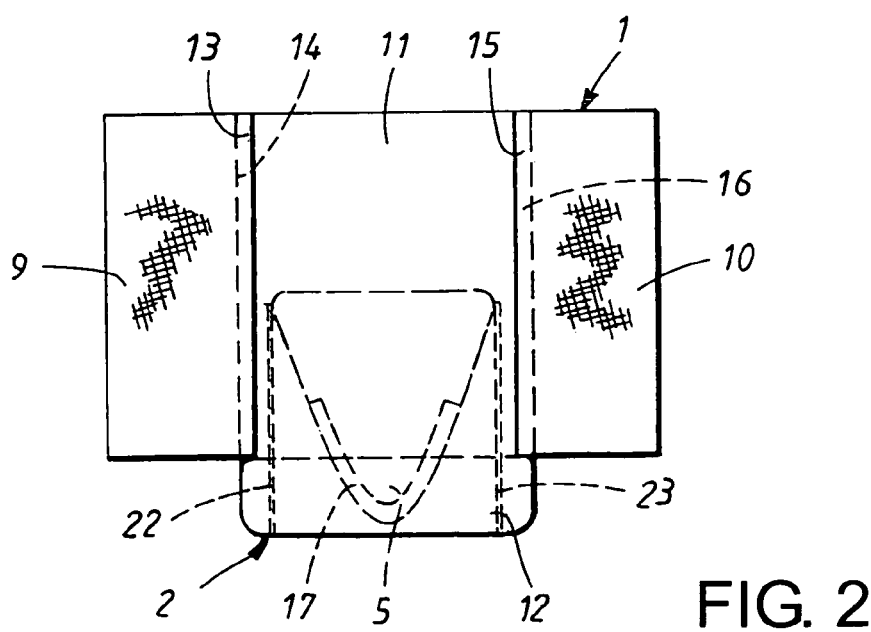
FIG. 2 shows diagrammatically in flat form an assembled product according to the first embodiment.
Figure 3:
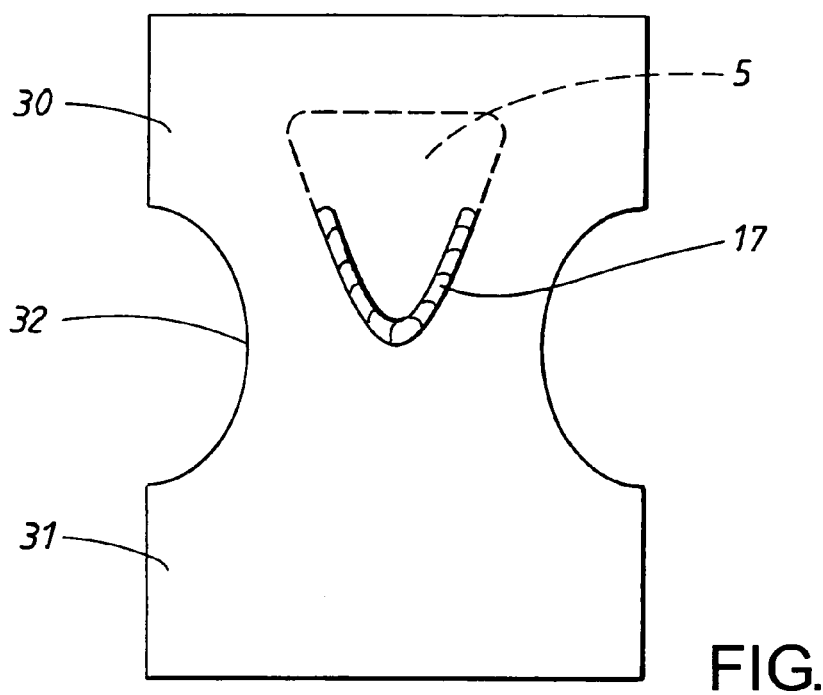
FIG. 3 shows diagrammatically in flat form a phase in the development of an absorbent product according to a second embodiment of the invention.

In FIG. 1, the arrows A and B are used to illustrate how the first and second pieces are folded for the formation of the pants-shaped absorbent product shown in FIGS. 2 and 3. The elastic piece 1 is folded in according to the shown arrows A to form the rear section 8 and side sections 9, 10 of the products, whereas the second piece is folded upwards according to the arrows B to form the front section 11 and crotch section 12 of the product.

The one end section 13 of the first piece is applied in slightly overlapping arrangement with a first side edge section 14 of the second piece and the second end section 15 of the first piece is correspondingly applied in slightly overlapping arrangement with a second side edge section 16 of the second piece. These overlapping parts are mutually connected, for example by means of bonding agent, heat bonding or ultrasonic bonding. Alternatively, the front section and the crotch section can be detachably applied along the said overlapping sections 13, 14 and 15, 16 respectively. A detachable connection of this kind can be constituted, for example, by a hook member (not shown), whereby the pants-like product can be opened and subsequently closed up again with the same fit and tightening.

On the liquid-permeable layer 3, at the narrower end section of the absorption body, a liquid barrier 17 is applied. In the illustrative embodiment shown in FIGS. 1 and 2, this is arranged to follow the contour of the lower, narrower end section of the absorption body and is applied in its entirety inside the said contour. The liquid barrier 17 is arranged to prevent urine emitted by the user from leaking from the surface of the absorption body towards the crotch section 12.

As stated above, the absorption body can be formed, for example, from cellulose fluff, possibly with highly absorbent material mixed in. The liquid barrier can be constituted by a moulding, which is formed from air-laid fibers such as cellulose fluff. As shown in FIGS. 1 and 2, this moulding is expediently applied so that it follows the contour of the narrower end section of the absorption body and on top of its surface. The liquid barrier can also be applied outside the absorption body and is in this case expediently applied directly adjacent to the contour of the absorption body.

The liquid barrier can be configured in many different ways, as will be evident from the continued description. It has proved expedient for the liquid barrier, at least during product usage and at least close to the middle of the absorption body in the transverse direction, to have a height of at least 5 mm, preferably 10-20 mm. For the product to work as intended, the liquid barrier needs to be positioned such that, during product usage, it is situated below the penis of the user. The liquid barrier must also be curved and convex in the direction of the crotch section 12. The fact that the barrier has a necessary height of at least 5 mm and is convexly curved in the direction of the crotch section means that the pad is very secure against leakage and liquid is prevented or inhibited from passing the liquid barrier 17 in the direction of the crotch section or in the lateral direction in which the liquid barrier with its upwardly curved sections constitutes an effective barrier.

In the embodiment according to FIGS. 1 and 2, the pants-like product is provided with pretensioned leg elastic 22, 23 in the crotch section, the leg elastic being intended, during product usage, to bring the side flaps, formed by the outer layer and the inner layer, on both sides of the absorption body into bearing contact against the leg of the user in his crotch region.

Figure 4:
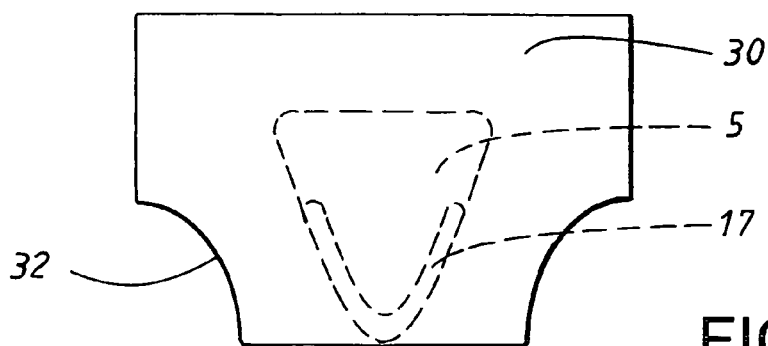
FIG. 4 shows diagrammatically in flat form an assembled product according to the second embodiment.

In FIGS. 3 and 4, another embodiment of a pants-like product is shown. The absorption body 5 and the liquid barrier 17 are configured in the same way as has been described above in connection with FIGS. 1 and 2. As can be seen from FIG. 3, the sheath for the absorption body, formed by the outer layer 4 and the inner layer 3, is shaped like an hourglass, having a front section 30, a rear section 31 and a crotch section 32. The side sections of the sheath in the front section are connected in a conventional manner to opposing side sections on the rear section to form pants according to FIG. 4. The sheath of the pants is conventionally configured with waist elastic (not shown) in order to hold the applied pants in place on the user and with leg elastic (not shown) for snug tightening of the sheath against the leg of the user in the crotch region.

The liquid barrier 17 can be formed together with the absorption body from air-laid fluff and applied inside the sheath. The liquid barrier and the absorption body can also be configured in one piece from a cast foam material, possibly with highly absorbent material mixed in. It can, of course, be an alternative to choose in this context a foam material which has very high absorbency and high holding capacity even under pressure loading. If the liquid barrier does not contain any direct liquid-barring layer, then high holding capacity is important.

A pants-like product according to FIGS. 3 and 4, instead of having a liquid barrier configured in one piece with the absorption body, can have a liquid barrier on the outer side of the inner layer 3. Liquid barriers of this type will be described in greater detail below in connection with a number of illustrative embodiments.

The absorbent product according to the invention does not need to be in the form of complete disposable pants, but can be constituted by a separate insert which can be used in combination with normal textile pants or in combination with special pants, matched to the insert, for repeated use.

Figure 5:
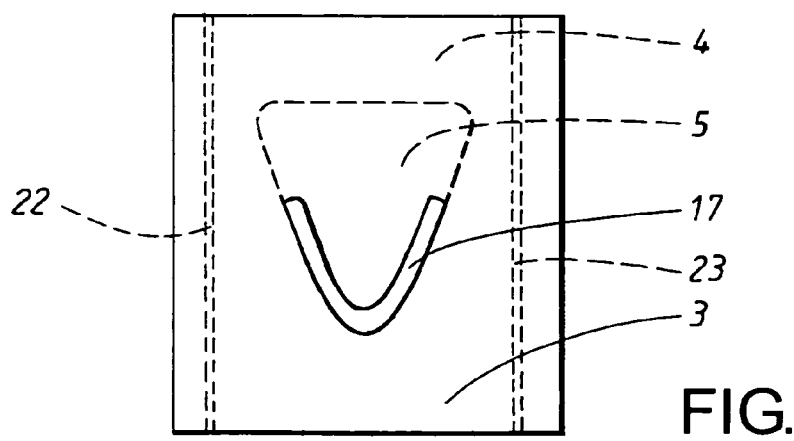
FIG. 5 shows in flat form a third embodiment of the product according to the invention.

An example of such an insert is shown in FIG. 5. The insert has an absorption body 5 enclosed in a rectangular sheath, consisting of a liquid-tight outer layer 4 and a liquid-permeable inner layer 3. To the outer side of the liquid-tight layer 4 are applied one or more fastening members (not shown) for detachable connection to a pair of interacting underpants. In the illustrative embodiment shown, the sheath is provided with pretensioned elastic 22, 23 on both sides of the absorption body. The liquid barrier 17 is V-shaped and applied so that it follows the contour of the absorption body 5.

Figure 6:
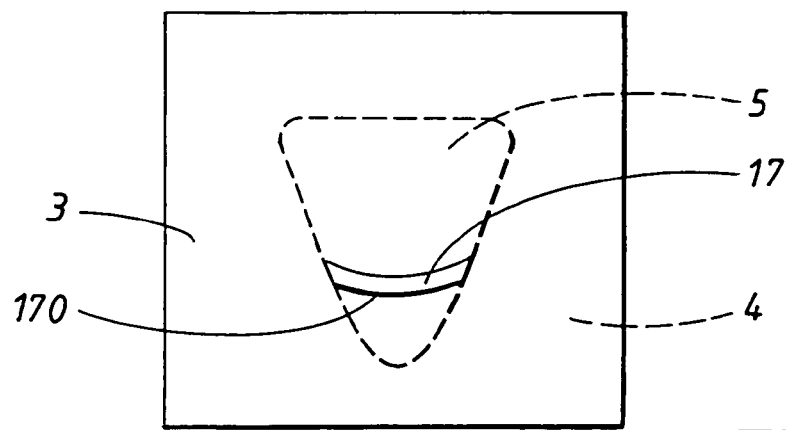
FIG. 6 shows in flat form a fourth embodiment of the product according to the invention.

In FIG. 6, an embodiment is shown which is somewhat modified in relation to the embodiment according to FIG. 5. The fundamental difference is that the liquid barrier 17 here has less curvature and is applied higher up on the absorption body 5. A lesser curvature means that a liquid barrier which is somewhat stiff can be more easily connected to the surface material, i.e., the inner layer 3. In the illustrative embodiment shown, the liquid barrier 17 can be constituted by a material strip which is flat in its basic form and is somewhat stiff and which is only fixed to the surface material along its lower, outer edge section 170. The liquid barrier will hence during product usage, since the fastening of the edge section 170 follows a curved path, lift up from the surface material and form a vertical liquid barrier. The liquid barrier 17 has here been shown applied higher up than in the illustrative embodiments above. One reason for this is that the liquid barrier must have a certain extent in the lateral direction in order to form an effective protection against liquid dispersion.

Figure 7:
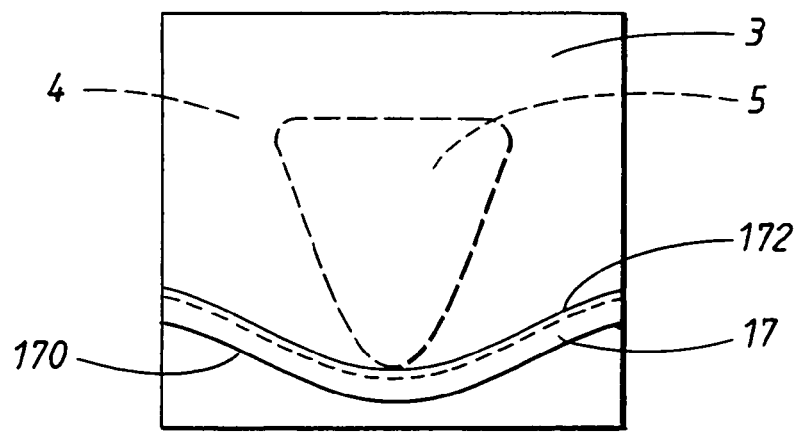
FIG. 7 shows in flat form a fifth embodiment of the product according to the invention.

In FIG. 7, an illustrative embodiment is shown which is somewhat modified in relation to the embodiment according to FIG. 6. Here, too, the liquid barrier 17 has less curvature than the liquid barriers in the embodiments according to FIGS. 1-5. In the embodiment according to FIG. 7, the liquid barrier 17 extends across the full extent of the insert in the lateral direction, thereby simplifying the product process in terms of the fitting of the liquid barrier. This is only fixed in the inner layer 3 along its lower, outer edge section 170 and is provided along its free edge section with a pretensioned elastic thread 172, which is intended to hold the liquid barrier in the raised state. In the embodiment shown in FIG. 7, it is, of course, important for the outer layer 4 to be liquid-tight.

Figure 8:
FIG. 8 shows diagrammatically an illustrative embodiment of a liquid barrier incorporated in the product according to the invention.

In FIG. 8, an illustrative embodiment is shown of a liquid barrier for a product according to the invention. The liquid barrier 17 is constituted by a roll formed from one or more band-shaped materials. For example, the roll can be formed from a hydrophobic non-woven material. Alternatively, the roll can be formed from a plastics film. A further example is a laminate of a liquid-tight film and a non-woven material. The roll is expediently so configured and consists of material of such a type that the roll is flexible and can be bent into the desired convex shape in the direction of the narrower end of the absorption body and applied to or in connection with the absorption body.

Figure 9A:
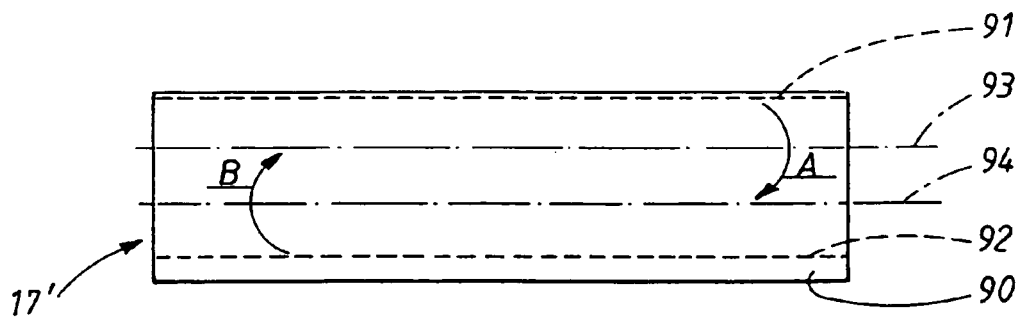
FIGS. 9a-9d show various phases in the development of a liquid barrier according to another illustrative embodiment.
Figure 9B:

FIGS. 9a-d show an illustrative embodiment of a liquid barrier for a product according to the invention and how the liquid barrier is made. FIG. 9a shows the basic material in the form of an elongated material piece consisting of, for example, hydrophobic non-woven material or a laminate of two or more layers. The material piece 17' is intended to be triple-folded into circumferential folds and in the illustrative embodiment shown has an edge section 90, which edge section, after the material piece is folded, is intended to be connected to the outer side of the folded material piece. The material piece in FIG. 1 has been provided with two longitudinal elastic threads 91, 92, which are applied in the pretensioned state, as shown in FIG. 9a, with one elastic thread 91 along the one edge section and with the other elastic thread 92 directly in front of the edge section 90. The material piece 17' is folded first along a longitudinal fold line 93, as shown by the arrow A, and then along a longitudinal fold line 94, as shown by the arrow B. The edge section 90 is next connected to the outer side of the folded material piece. The folded material piece 17' is shown in FIG. 9b. Following the folding, the elastic threads 91, 92 are situated along opposing edge sections. For the formation of the V-shaped liquid barrier 17 shown in FIG. 9c, the material piece 17' in FIG. 9b is folded in the middle at a 45° angle. This angle can, of course, be varied in order to obtain the desired inclination of the arms of the V-shaped liquid barrier.

Figure 9C:
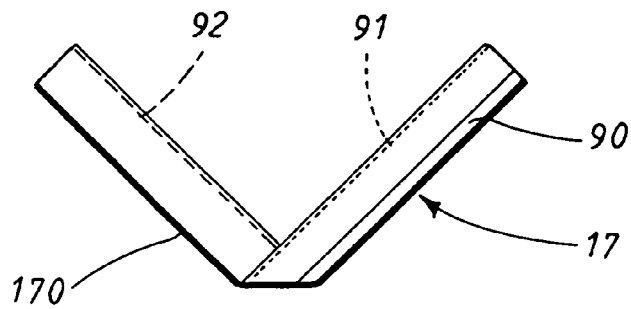

The V-shaped liquid barrier according to FIG. 9c is intended to be connected along the whole of its length by its lower outer edge section 170 to the inner layer of the absorbent product and expediently along the contour of the lower part of the absorption body, as shown in the embodiment according to FIG. 5. The elastic sections which are situated at the edge sections connected to the inner layer of the absorbent product will become inactive as a result of the connection and only the elastic sections along the free edge sections of the liquid barrier continue to be active in raising the liquid barrier. Those edge sections 170 of the liquid barrier which are connected to the inner layer 3 have been marked in FIG. 9c with bolder lines.

Figure 9D:
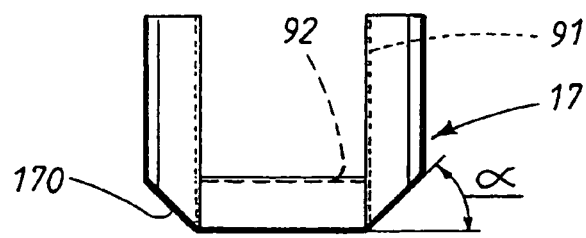

Alternatively, a material strip 17' according to FIG. 9b can be folded into a U-shape, as shown in FIG. 9d. The fold angle α is in the drawing 45°. This angle can be reduced if a liquid barrier is desired in which the arms of the U-shape are more outwardly inclined. The U-shaped liquid barrier is intended to be connected along the edge sections 170 marked in the drawing with thicker lines. Only those pieces of the elastic threads 91, 92 which are marked in FIG. 9d will be active in raising the liquid barrier. Other sections have been disabled as a result of the connection to the inner layer 3.

Figure 10:
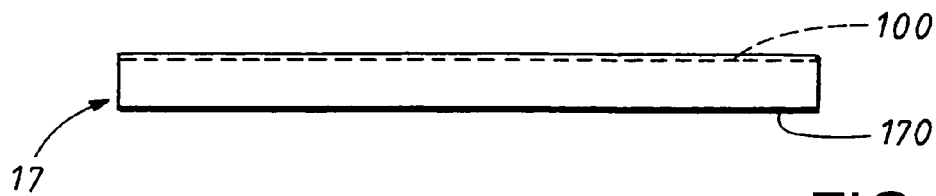
FIG. 10 shows diagrammatically a third illustrative embodiment of a liquid barrier in a product according to the invention.

In FIG. 10 a liquid barrier in the form of a single elongated material strip is shown, for example made of hydrophopic non-woven material, which is intended to be folded or bent into suitable shape prior to being applied to the inner layer 3 of a product according to the invention. The elongated material strip can also be constituted by a liquid-tight foam material. The material strip can be provided with a pretensioned longitudinal elastic thread 100, which is intended to hold the liquid barrier in the raised state. If the material in the elongated strip has a certain stiffness and the material strip is fastened along its lower edge section 170, marked in the drawing with a thicker line, the elastic thread 100 is unnecessary in the curved state, since the barrier is raised by its own stiffness, firstly by a bit after the material strip is fastened and secondly by a further bit when the product as a whole is bent as it is applied to the user.

Figure 11:
FIG. 11 shows diagrammatically a fourth illustrative embodiment of a liquid barrier in a product according to the invention.

FIG. 11 shows a curved material strip cut out in flat form and made of, for example, a plastics film, a foam material or a laminate of non-woven material and a plastics film. The material strip is intended to be connected to the outer layer 3, for example as shown in FIG. 6, along the edge sections 170 marked in FIG. 11 with thicker lines. Expediently, the material strip has such inherent stiffness that the liquid barrier formed by the strip is raised when the product is taken into use and applied to the user.

Figure 12:
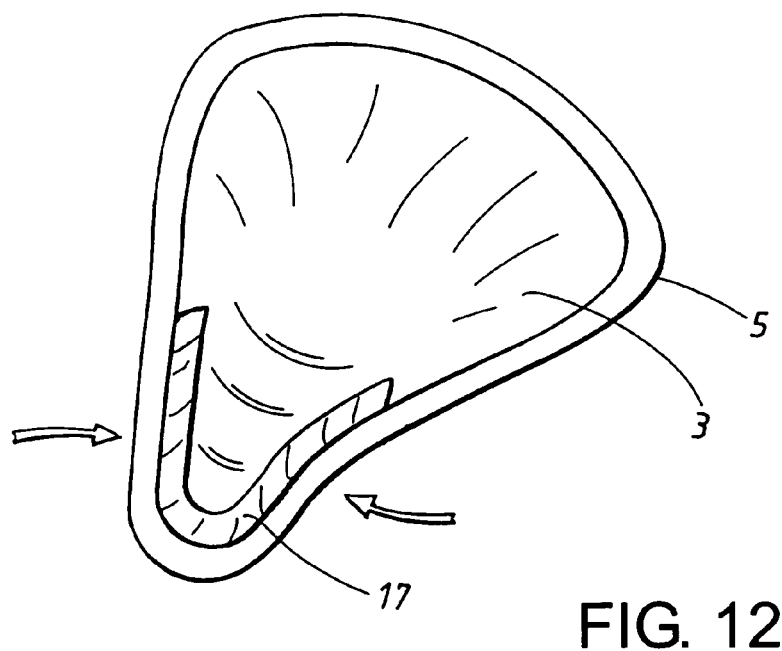
FIG. 12 shows diagrammatically in perspective a further embodiment of the liquid barrier and in the state of use.

FIG. 12 illustrates how a liquid barrier 17 in the form of a flat material strip is intended to perform in the usage position when the leg of the user, in his crotch section, presses on the absorption body in the direction of the arrows in FIG. 12. The liquid barrier 17 is raised and prevents or inhibits urine emitted by the user from leaking out into the crotch region.

Figure 13:
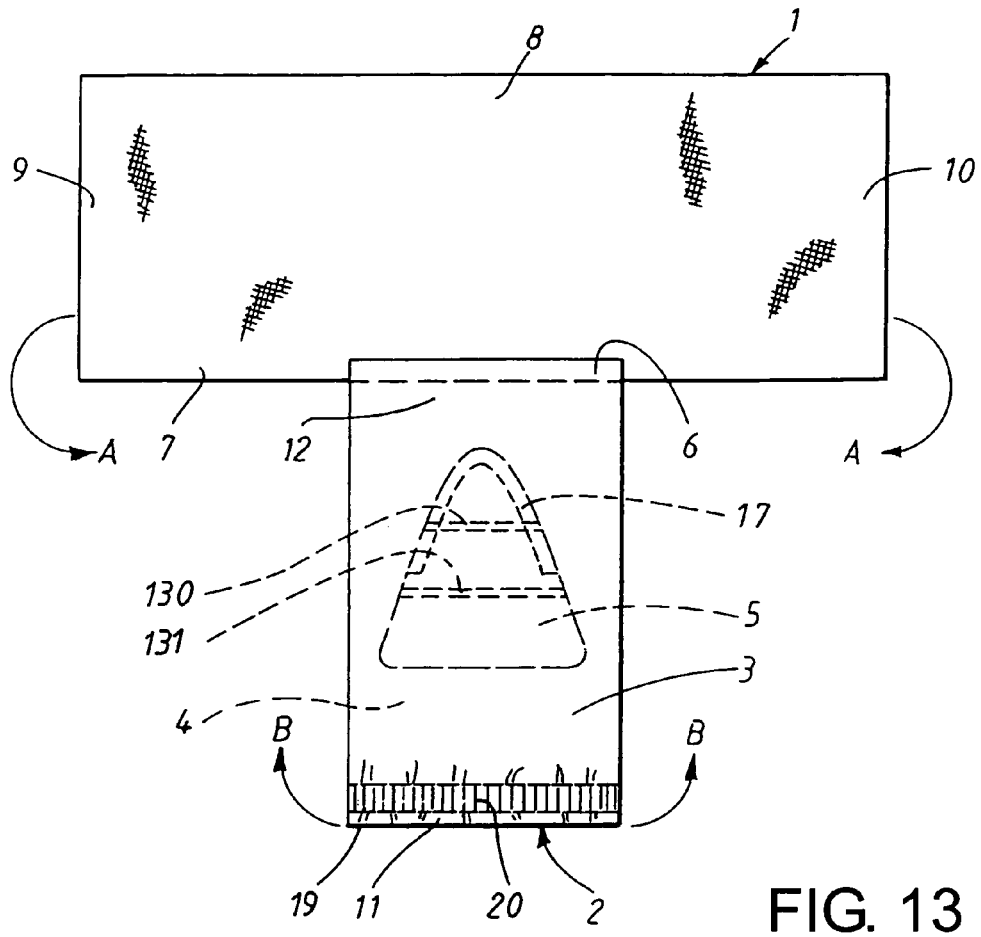
FIG. 13 shows diagrammatically a phase in the development of a further embodiment of the product according to the invention.
Figure 14:
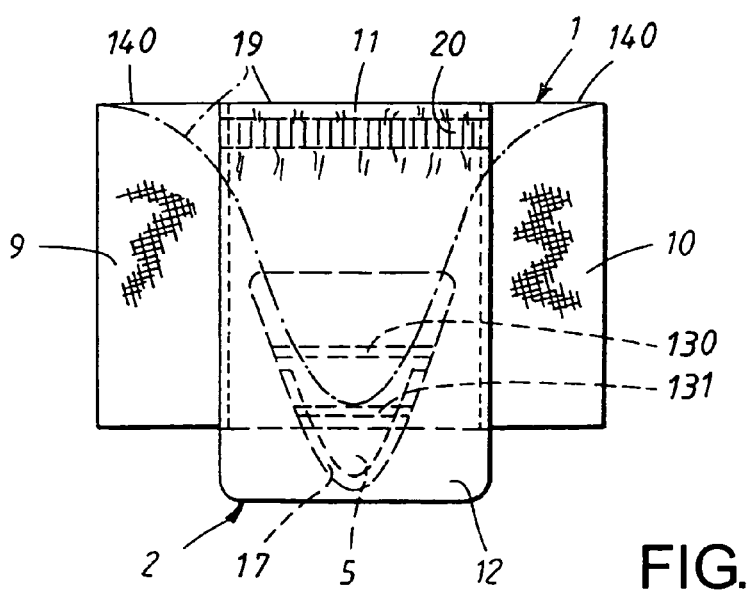
FIG. 14 shows diagrammatically in flat form an assembled product according to the embodiment shown in FIG. 13.

FIGS. 13 and 14 show a pants-like product which has much in common with the embodiment according to FIGS. 1 and 2. Components identical to or corresponding to similar parts as in the embodiment according to FIGS. 1 and 2 have in FIGS. 13 and 14 been provided with the same reference notations. The embodiment according to FIGS. 13 and 14 differs from the embodiment shown in FIGS. 1 and 2 by the fact that the front section has been provided with at least one elastic member 20, which, during product usage, enables the front section 11 of the product to be pulled down, counter to the action of the said elastic member 20, to a position in which the upper limit edge 19 of the front section in the middle region of the front section is situated below the penis of the user, at the same time as the upper limit edge of the front section in the two outer edge regions 140 of the front section is arranged to be held in place around the waist of the user. The absorbent material is configured with one or more deformation zones 130, 131, which enable those parts of the absorption body which, during product usage, are situated above and over the penis of the user to be drawn down together with the rest of the front section when the front section of the product is pulled down. The front section of the product and the absorbent element are arranged to be returned by the elastic member to their original usage position.

In previously known incontinence pads for men, the user has, in practice, been unable to visit urinals. It is naturally inconceivable for a man, in connection with a toilet visit at a urinal, to pull down a whole incontinence pad and thereby reveal private and embarrassing problems to those around him. With a pad according to the embodiment shown in FIGS. 13 and 14, this problem has been eliminated. In FIG. 14, the dash-dot line 19 has been used to illustrate the extent to which the front section of the product is pulled down in connection with a visit to a urinal. In the illustrative embodiment shown, the deformation zones 130 and 131 are constituted by two fold notches. When the front section 11 of the product is pulled down, the absorption body 5 is folded firstly along the deformation zone 130 and then, upon continued pulling down, along the deformation zone 131. The liquid barrier characteristic of the present invention has been denoted by 17.

Figure 15:
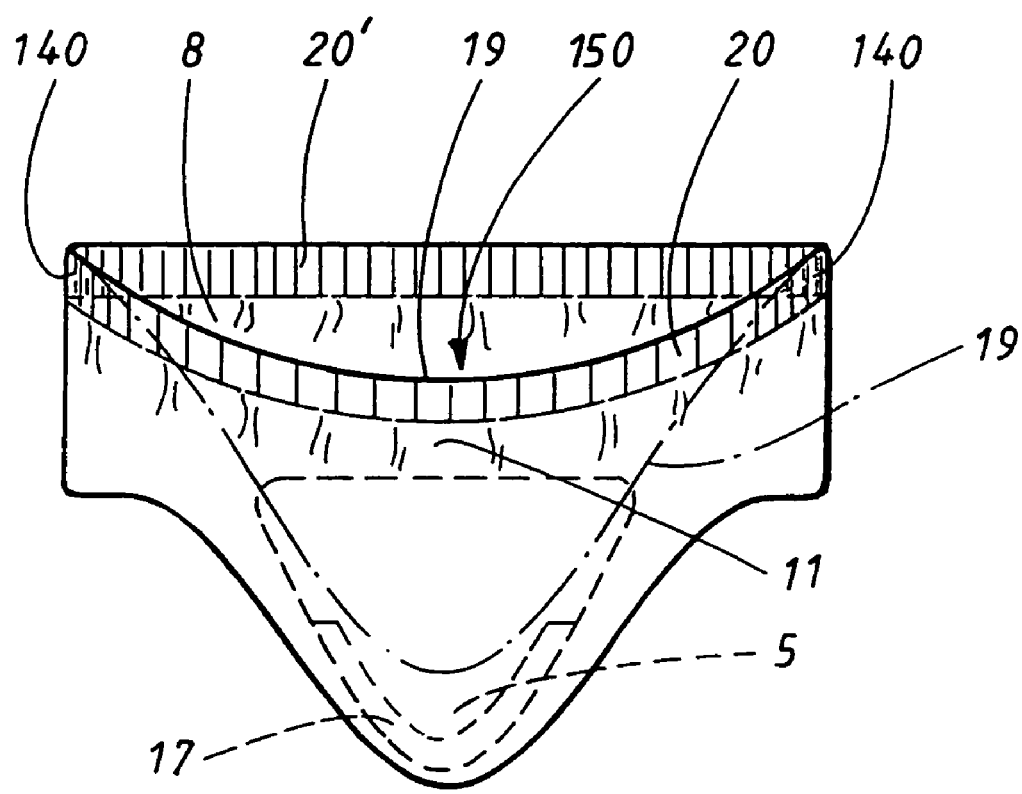
FIG. 15 shows diagrammatically and in flat form another embodiment of a product according to the invention.

In FIG. 15, an illustrative embodiment is shown which is somewhat modified in relation to the embodiment according to FIGS. 13 and 14. Components which are corresponded to by the same or similar parts as in FIGS. 13 and 14 have been provided with the same reference notations. Compared with the illustrative embodiment according to FIG. 14, the pants-like product according to FIG. 15 has a more conventional pants cut. The fundamental difference is the low cut of the front section 11 of the pants. This has been marked in the figure with the reference numeral 150. The low cut at the front at 150 makes it easier for the upper limit edge of the front section to be pulled down to a position below the penis of the user. In order to reduce the risk of the pants being pulled down in their entirety as the front section 11 is pulled down by the user in a visit to a urinal, the waist section 20 can at the front have higher elastic stretchability than the rear section 20' of the waist elastic.

The invention is not limited to the above-stated illustrative embodiments, but rather a number of modifications are possible within the scope of the following patent claims.

In the illustrative embodiments shown above, the absorption body is essentially triangular and tapered in the direction of the crotch section of the product. An absorption body which tapers in the direction of the crotch section is comfortable for the user, but other shapes, such as rectangular absorption bodies which are not tapered in the said direction, are also conceivable within the scope of the present invention.

The invention is not limited to the illustrative embodiments described above, but a number of modifications are possible within the scope of the patent claims below.

The invention claimed is:

1. An absorbent product for men, comprising
a front section,
a rear section, and
a crotch section between the front and rear sections,
an absorption body which tapers towards one end from a front section of the product towards the crotch section of the product and which is enclosed in a sheath comprising a liquid-tight layer on a side of the absorption body facing away from the user during use and a liquid-permeable layer on an opposite side of the absorption body, both of which layers extend beyond the absorption body and are mutually joined together, and
the absorption body is arranged to extend, during product usage, from the front section of the product in the direction of the crotch section and is adapted to extend with its narrower end section to slightly below the penis of the user,
on the liquid-permeable layer, at the narrower end section of the absorption body, a liquid barrier is applied, which is arranged to prevent urine emitted by the user from leaking from the surface of the absorption body towards the crotch region of the user.

2. The absorbent product according to claim 1, wherein the absorbent product is an insert adapted for use with underpants and the absorbent product is provided with one or more fastening members on an outer side of the liquid-tight layer, which fastening members are adapted to hold the absorbent product in place inside the underpants.

3. The absorbent product according to claim 1, wherein the product as a whole has a pants shape, the front section and the rear section being adapted to surround a waist of the user, and the front or rear section is provided with waist elastic which is adapted to hold the absorbent product in place on the user.

4. The absorbent product according to claim 3, wherein the front section has at least one elastic member, which, during product usage, enables the front section of the product to be pulled down, counter to the action of the elastic member, to a position in which an upper limit edge of the front section in the middle region of the front section is situated below the penis of the user, at the same time as the upper limit edge of the front section in the two outer edge regions of the front section is arranged to be held in place around the waist of the user, in that the absorption body is configured with one or more deformation zones, which enable those parts of the absorption body which, during product usage, are situated above and over the penis of the user to be drawn down together with the rest of the front section when the front section of the product is pulled down, and the front section of the product and the absorption body are arranged to be returned by the elastic member to their original usage position.

5. The absorbent product according to claim 3, wherein the waist elastic is formed from an elastic first piece which, in the extended state, is essentially rectangular and which is adapted to partially surround the trunk of the user and form the rear section and side sections of the pants product, a second piece, incorporated in the product, is configured to form the front section and crotch section of the pants product, the second piece is elongated with two opposing end edges and two opposing longitudinal edges, the width of the second piece, at least at the crotch section, is less than the length of the first piece, the second piece with its longitudinal direction is arranged perpendicularly to the longitudinal direction of the first piece and is connected by a first end section to the one longitudinal edge section of the first piece and centrally on this, the one end section of the first piece is connected to a first side edge section of the second piece, and the second end section of the first piece is correspondingly connected to a second side edge section of the second piece, and the absorption body applied, in its entirety, on the second piece.

6. The absorbent product according to claim 1, wherein the liquid barrier is arranged to follow the contour of the lower, narrower end section of the absorption body and is applied in its entirety inside the said contour.

7. The absorbent product according to claim 1, wherein the liquid barrier crosses the absorption body close to its narrower end and the liquid barrier is convex in the direction of the said end.

8. The absorbent product according to claim 7, wherein the liquid barrier extends in the lateral direction beyond the absorption body and in the transverse direction spans the whole of the absorbent product.

9. The absorbent product according to claim 1, wherein the liquid barrier, at least during product usage and at least close to the middle of the absorption body in the transverse direction, has a height of at least 5 mm.

10. The absorbent product according to claim 1, wherein the liquid barrier, at least during product usage and at least close to the middle of the absorption body in the transverse direction, has a height of at least 10 mm.

11. The absorbent product according to claim 1, wherein the liquid barrier, at least during product usage and at least close to the middle of the absorption body in the transverse direction, has a height of at least 20 mm.

12. The absorbent product according to claim 1, wherein the liquid barrier is fixed in the rest of the absorbent product only along its outer edge section and inner-situated sections of the liquid barrier are arranged to be raised from the liquid-permeable layer during product usage.

13. The absorbent product according to claim 1, wherein the liquid barrier is constituted by a roll formed from one or more band-shaped materials, which roll is bent into a convex shape in the direction of the narrower end of the absorption body.

14. The absorbent product according to claim 1, wherein the liquid barrier is constituted by a number of circumferential folds of one or more band-shaped materials, which liquid barrier, following the formation of the folds, is elongated in the direction of the fold lines forming the folds, and the liquid barrier is folded or bent into shape.

15. The absorbent product according to claim 14, wherein the elongated liquid barrier is folded in the middle along a transverse oblique line, at an angle of 45°, in relation to the longitudinal direction to form a V-shaped liquid barrier with the point of the V against the crotch section.

16. The absorbent product according to claim 14, wherein the elongated liquid barrier is folded at two places along transverse lines along an acute angle, viewed from the lower limit edge of the liquid barrier in the applied position, to form an essentially U-shaped liquid barrier with the base of the U against the crotch section.

17. The absorbent product according to claim 16, wherein the acute angle is less than 45°.

18. The absorbent product according to claim 13, wherein the band-shaped material consists of non-woven, or of a laminate of non-woven material and a plastics film.

19. The absorbent product according to claim 12, wherein the liquid barrier is constituted by a single material strip which has been folded or bent into suitable shape before being applied.

20. The absorbent product according to claim 19, wherein the single material strip is a hydrophobic non-woven material.

21. The absorbent product according to claim 14, wherein the liquid barrier, on its free longitudinal edge section, is provided with a pretensioned longitudinal elastic element, which element is adapted to hold the liquid barrier in the raised state during product usage.

22. The absorbent product according to claim 21, wherein the pretensioned longitudinal elastic element is an elastic thread.

23. The absorbent product according to claim 14, wherein the liquid barrier has an inherent stiffness of such magnitude that a liquid barrier applied in the folded or bent state, by virtue of its own inherent stiffness in the bent or folded state during product usage, is held with its free longitudinal edge section in the raised state.

24. The absorbent product according to claim 1, wherein the absorption body is formed from cellulose fluff, with highly absorbent material mixed in, and the liquid barrier is constituted by a moulding, which is formed from air-laid cellulose fluff fibers, and this moulding is applied so that it follows the contour of the narrower end section of the absorption body on or directly outside this.

25. The absorbent product according to claim 1, wherein the liquid barrier is constituted by a foam material which has been cast or folded into the desired shape.

26. An absorbent product for men, comprising:
a front section,
a rear section, and
a crotch section between the front and rear sections,
an absorption body which tapers from a wide end at the front section of the product towards a narrow end at the crotch section of the product and which is enclosed in a sheath comprising a liquid-tight layer on a side of the absorption body facing away from the user during use and a liquid-permeable layer on an opposite side of the absorption body, both of which layers extend beyond the absorption body and are mutually joined together, and
the absorption body is arranged to extend, during product usage, from the front section of the product in the direction of the crotch section and is adapted to extend with its narrow end section to slightly below the penis of the user,
a liquid barrier is arranged at the narrow end section of the absorption body so as to prevent urine emitted by the user from moving beyond the absorption body towards the crotch region of the user.

27. The absorbent product according to claim 26, wherein the absorbent product is an insert adapted for use with underpants and the absorbent product is provided with one or more fastening members on an outer side of the liquid-tight layer, which fastening members are adapted to hold the absorbent product in place inside the underpants.

28. The absorbent product according to claim 26, wherein the product as a whole has a pants shape, the front section and the rear section being adapted to surround a waist of the user, and the front or rear section is provided with waist elastic which is adapted to hold the absorbent product in place on the user.

29. The absorbent product according to claim 1, wherein the liquid barrier is liquid impermeable.

30. The absorbent product according to claim 26, wherein the liquid barrier is liquid impermeable.

31. The absorbent product according to claim 30, wherein the product as a whole has a pants shape, the front section and the rear section being adapted to surround a waist of the user, and the front or rear section is provided with waist elastic which is adapted to hold the absorbent product in place on the user.

32. The absorbent product according to claim 31, wherein the liquid barrier is a separate piece from the absorption body.

33. The absorbent product according to claim 1, wherein the liquid barrier is a separate piece from the absorption body.

34. An absorbent product for men, comprising:
a front section,
a rear section, and
a crotch section between the front and rear sections,
an absorption body which tapers from a wide end at the front section of the product to a narrow end towards the crotch section of the product and which is enclosed in a sheath comprising a liquid-tight layer on a side of the absorption body facing away from the user during use and a liquid-permeable layer on an opposite side of the absorption body, both of which layers extend beyond the absorption body and are mutually joined together, and
the absorption body is arranged to extend, during product usage, from the front section of the product in the direction of the crotch section and is adapted to extend with its narrow end section slightly below the penis of the user,
at the narrow end section of the absorption body or between the narrow end and the wide end of the absorption body, a liquid barrier is arranged either between the liquid-tight layer and the liquid-permeable layer or on the liquid-permeable layer, the liquid barrier is arranged to prevent urine emitted by the user from moving beyond the narrow end towards the crotch region of the user.

35. The absorbent product according to claim 34, wherein the liquid barrier is arranged between the liquid-tight layer and the liquid-permeable layer.

36. The absorbent product according to claim 13, wherein the band-shaped material consists of hydrophobic non-woven material or of a laminate of non-woven material and a plastics film.

* * * * *